US00PP25080P2

(12) United States Plant Patent
Pavlich

(10) Patent No.: US PP25,080 P2
(45) Date of Patent: Nov. 18, 2014

(54) ***BEGONIA* PLANT NAMED 'COOL BREEZE ROUGE'**

(50) Latin Name: ***Begonia* hybrid**
Varietal Denomination: Cool Breeze Rouge

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 35 days.

(21) Appl. No.: 13/986,388

(22) Filed: Apr. 26, 2013

(51) Int. Cl.
*A01H 5/00* (2006.01)

(52) U.S. Cl.
USPC ..... Plt./343

(58) Field of Classification Search
CPC ..... A01H 5/0238
USPC ..... Plt./343
See application file for complete search history.

*Primary Examiner* — June Hwu
*Assistant Examiner* — Keith Robinson
(74) *Attorney, Agent, or Firm* — Klarquist Sparkman, LLP

(57) ABSTRACT

A new and distinct form of *Begonia* plant characterized by broad, palmately lobed leaves of showy silver with a green spot by the petiole and a rose blush, red leaf backs, a bushy habit, clusters of cherry pink flowers in winter to early spring, and excellent vigor.

1 Drawing Sheet

Botanical denomination: *Begonia* hybrid.
Variety designation: 'Cool Breeze Rouge'.
Parentage: *Begonia hemsleyana*×*Begonia* U489.
Cross Reference to: *Begonia* hybrids 'Cool Breeze Pewter' (U.S. Plant patent application Ser. No. 13/987,232) and 'Cool Breeze Glacier' (U.S. Plant patent application Ser. No. 13/986,393).

BACKGROUND

The present invention relates to a new and distinct cultivar of *Begonia*, of the family Begoniaceae, and given the cultivar name, 'Cool Breeze Rouge'. This plant originated from planned breeding program for a colorful series of landscape *Begonia*. The new cultivar originated from a cross between *Begonia hemsleyana*, as the seed parent, and *Begonia* U489, as the pollen parent. This selection is uniquely characterized by:

1. broad, palmately lobed leaves,
2. showy silvered leaves with green spot by the petiole and a rose blush,
3. red leaf backs,
4. a bushy habit,
5. clusters of cherry pink flowers in winter to early spring, and
6. excellent vigor.

Compared to the seed parent *Begonia hemsleyana*, an unpatented plant, the new cultivar has leaves palmately lobed rather than palmately compound and heavily silvered rather than silver spotted.

Compared to the pollen parent, *Begonia* U489, an unpatented plant, the new cultivar is broader in habit, better branched, and with leaves that lobed rather than entire and with a rouge blush rather than no blush.

Compared to *Begonia* 'Metallic Mist', U.S. Plant Pat. No. 19,567, the new cultivar is larger and bushier, with larger, flatter leaves that have a green spot near the petiole and a rose blush rather than dark veins with silver.

Compared to *Begonia* 'Cool Breeze Pewter', U.S. Plant patent application Ser. No. 13/987,232, the new cultivar has a rose blush in cool temperatures rather than staying all silver.

Compared to *Begonia* 'Cool Breeze Glacier', U.S. Plant patent application Ser. No. 13/986,393, the new cultivar has a leaves that are pewter overall with rose blush in cool temperatures and a dark green spot at the leaf base rather than having strongly interveinally silver leaves. The new variety has been reproduced only by asexual propagation (leaf cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the foliage color and habit of *Begonia* 'Cool Breeze Rouge' in cool temperatures.

FIG. 2 shows the foliage color of the new variety in warm temperatures in Canby. Oreg.

DETAILED PLANT DESCRIPTION

The following is a detailed description of the new *Begonia* cultivar based on observations of 14 month-old specimens grown in one gallon containers in a greenhouse in January in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, 5$^{th}$ edition, 2007.

Plant:

*Type*.—Herbaceous rhizomatous perennial.

*Form*.—Clumping, caulescent.

*Cold hardiness*.—USDA Zone 10.

*Size*.—Grows to 40 cm tall and 45 cm wide.

*Vigor*.—Excellent.

*Roots and rooting*.—Roots appear on leaf cuttings in 2 weeks; fine, fibrous, and white in color.

Stem:

*Type*.—Upright.

*Size*.—Grows to 19 cm long and 16 mm wide.

*Internodes*.—From 1 to 6 cm long.

*Lateral branches*.—None.

*Surface*.—Pubescent.

*Color*.—Greyed Purple 187A to 187B.

Leaf:

*Type*.—Simple.

*Arrangement*.—Alternate.

*Number*.—About 150.

*Shape*.—Orbicular to reniform.

*Lobing/division*.—Palmately 7 lobed.

*Venation*.—Palmate, topside Green 137A near petiole to Greyed Green188A near margin, bottom side Greyed Purple 187B.

*Margins*.—Senate.

*Apex*.—Acuminate.

*Base*.—Sagittate.

*Blade size*.—Grows to 19 cm wide and 19 cm long.

*Leaf strength*.—Excellent, tough, leathery.

*Surface texture*.—Glabrous on top and pubescent on bottom.

*Stipules*.—Deciduous, ovate-lanceolate, 22 mm long and 12 mm wide, apex acuminate and cuspidate, base clasping, entire, back side pubescent, inside glabrous, both sides Greyed Red181B.

*Petiole description*.—Grows to 24 cm long and 7 mm wide, succulent, pubescent, Greyed Orange 177A.

*Leaf color*.—Top side closest to Greyed Green 188A, blushed Red Purple 64A in warm temperatures, and with spot near petiole Green 137A; bottom side Greyed Purple 187B.

Inflorescence:

*Type*.—Axillary, bisexual, cymose.

*Number of flowers per cyme*.—Usually 6.

*Peduncle description*.—Grows 13 cm long and 4 mm wide, pubescent, fleshy, of good strength, Greyed Orange 178B; with 2 opposite, dehiscent petiolate leaf-bracts below each cyme, deciduous, ovate-lanceolate, 22 mm long and 12 mm wide, apex acuminate and cuspidate, entire, back side pubescent, inside glabrous, both sides Greyed Red 181B.

*Pedicel description*.—Grow to 20 mm long, 1.5 mm wide, fleshy, of good strength, pubescent, Red 48C.

*Bloom period*.—Late fall to early winter in Canby, Oreg.

Flower bud:

*Size*.—Staminate flowers 12 mm long and 8 mm wide prior to opening; pistillate flowers are 20 mm deep and 18 mm wide prior to opening.

*Shape*.—Teardrop.

*Surface texture*.—Pubescent.

*Color*.—Red Purple 68B on tepal area, Red Purple 69A on ovary.

Flower:

*Type*.—Monoecious, bilaterally symmetrical.

*Pistillate flower*.—Grows to 20 mm deep and 35 mm wide overall; 5 fleshy tepals, grow to 16 mm long and 11 mm wide, obovate, tip and base obtuse to acute, margins entire, glabrous on inside and pubescent on outside, inside Red Purple 73C and outside center 73B to sides 73C; pistil 1, 19 mm long, ovary to 22 mm wide and 12 mm deep, three winged, two equal and one longer, Orange 27B with edges Yellow Green 150C, style 3 branched, 2 mm long and Greyed Yellow 161B, stigma 2 branched and twisted, stigma 5 mm deep and 10 mm wide overall, Yellow Green 151A.

*Staminate flower*.—12 mm deep and 25 mm wide, 4 tepals, Red Purple 73C inside and 73B outside, 2 larger outer tepals 16 mm long and 14 mm wide, cupped, ovate, margin entire, tip obtuse, base cuneate; pubescent outside and glabrous inside, 2 inner tepals grow to 12 mm long and 7 mm wide, oblanceolate, entire, tip obtuse, base attenuate; stamen many in a globular head 6 mm in diameter, filaments less than 1 mm long, anthers 1.5 mm long and Red Purple 65D, anthers and pollen Yellow 11A.

*Fragrance*.—None

*Lastingness*.—A cyme blooms for about 4 weeks on the plant, flowers are self-cleaning Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

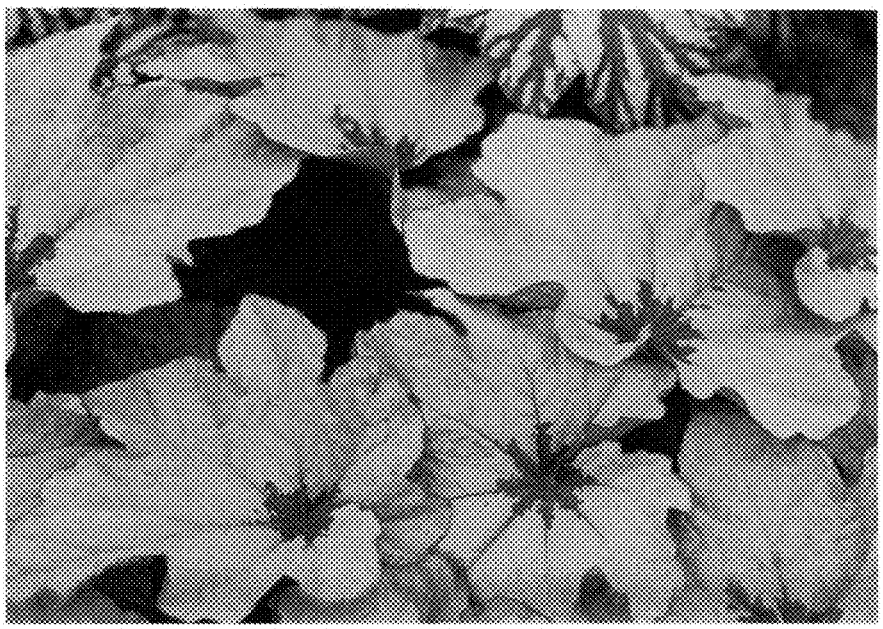

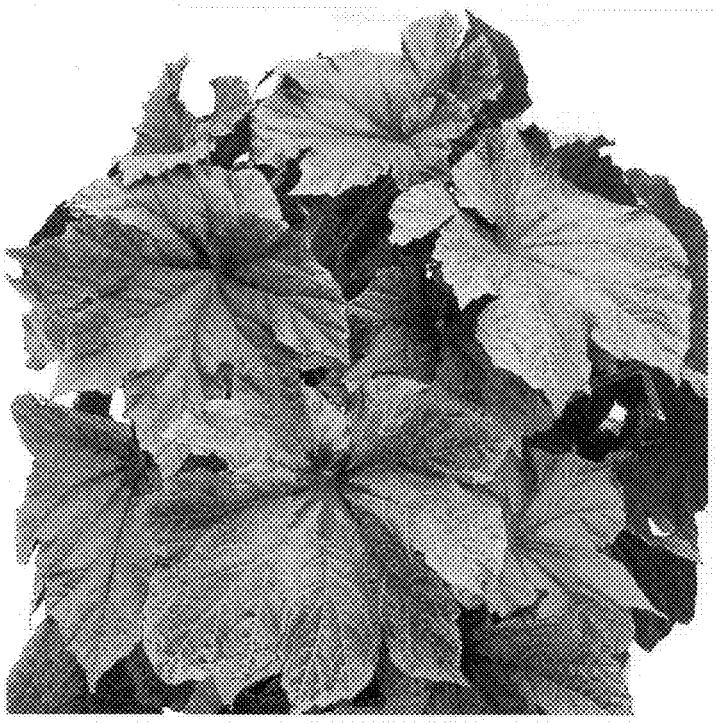
FIG 1 left
FIG 2 below